US00PP24929P2

(12) United States Plant Patent
Baijens

(10) Patent No.: US PP24,929 P2
(45) Date of Patent: Sep. 23, 2014

(54) *LAVANDULA* PLANT NAMED 'SUPERBLUE'

(50) Latin Name: *Lavandula angustifolia*
Varietal Denomination: SuperBlue

(75) Inventor: Martijn Baijens, Grootebroek (NL)

(73) Assignee: Ball Horticultural Company, West Chicago, IL (US)

( * ) Notice: Subject to any disclaimer, the term of this patent is extended or adjusted under 35 U.S.C. 154(b) by 275 days.

(21) Appl. No.: 13/507,929

(22) Filed: Aug. 8, 2012

(51) Int. Cl.
*A01H 5/00* (2006.01)

(52) U.S. Cl.
USPC ..... Plt./445

(58) Field of Classification Search
USPC ..... Plt./445
See application file for complete search history.

*Primary Examiner* — Annette Para
(74) *Attorney, Agent, or Firm* — Audrey Charles

(57) ABSTRACT

A new and distinct cultivar of *Lavandula* plant named 'SuperBlue', characterized by its deep violet-blue colored flowers, medium green-colored foliage, and moderately vigorous, mounded-compact growth habit.

1 Drawing Sheet

Latin name of genus and species of plant claimed: *Lavandula angustifolia.*

Variety denomination: 'SuperBlue'.

BACKGROUND OF THE INVENTION

The present invention relates to a new and distinct cultivar of *Lavandula* plant botanically known as *Lavandula angustifolia* and hereinafter referred to by the cultivar name 'SuperBlue'.

The new cultivar originated in a controlled breeding program in Venhuizen, The Netherlands during July 2005. The objective of the breeding program was the development of *Lavandula* cultivars that are free-flowering with a mounded-compact growth habit.

The new *Lavandula* cultivar is the result of cross-pollination. The female (seed) parent of the new cultivar is the proprietary *Lavandula angustifolia* breeding selection coded 1313-01, not patented, characterized by its violet-blue colored flowers, medium green-colored foliage, and mounded-compact growth habit. The male (pollen) parent of the new cultivar is the proprietary *Lavandula angustifolia* breeding selection coded 1254-01, not patented, characterized by its violet-blue colored flowers, medium green-colored foliage, and mounded-compact growth habit. The new cultivar was discovered and selected as a single flowering plant within the progeny of the above stated cross-pollination during July 2006 in a controlled environment at Venhuizen, The Netherlands.

Asexual reproduction of the new cultivar by terminal stem cuttings since July 2006 at Venhuizen, The Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'SuperBlue' as a new and distinct cultivar of *Lavandula* plant:

1. Deep violet-blue colored flowers;
2. Medium green-colored foliage; and
3. Moderately vigorous, mounded-compact growth habit.

Plants of the new cultivar differ from plants of the female parent primarily in having a deeper violet-blue colored flower. Plants of the new cultivar differ from plants of the male parent primarily in having a longer spike length.

Of the many commercially available *Lavandula* cultivars, the most similar in comparison to the new cultivar is 'Blue Royalty', U.S. Plant Pat. No. 20,657. However, in side-by side comparisons, plants of the new cultivar differ from plants of 'Blue Royalty' in at least the following characteristics:

1. Plants of the new cultivar have a flower color that is darker and more blue than plants of 'Blue Royalty'; and
2. Plants of the new cultivar have shorter peduncles than plants of 'Blue Royalty'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'SuperBlue'. Plants were transplanted from greenhouse-grown one-gallon containers and field grown for approximately 8 weeks in West Chicago, Ill.

DETAILED BOTANICAL DESCRIPTION

Figure 1:
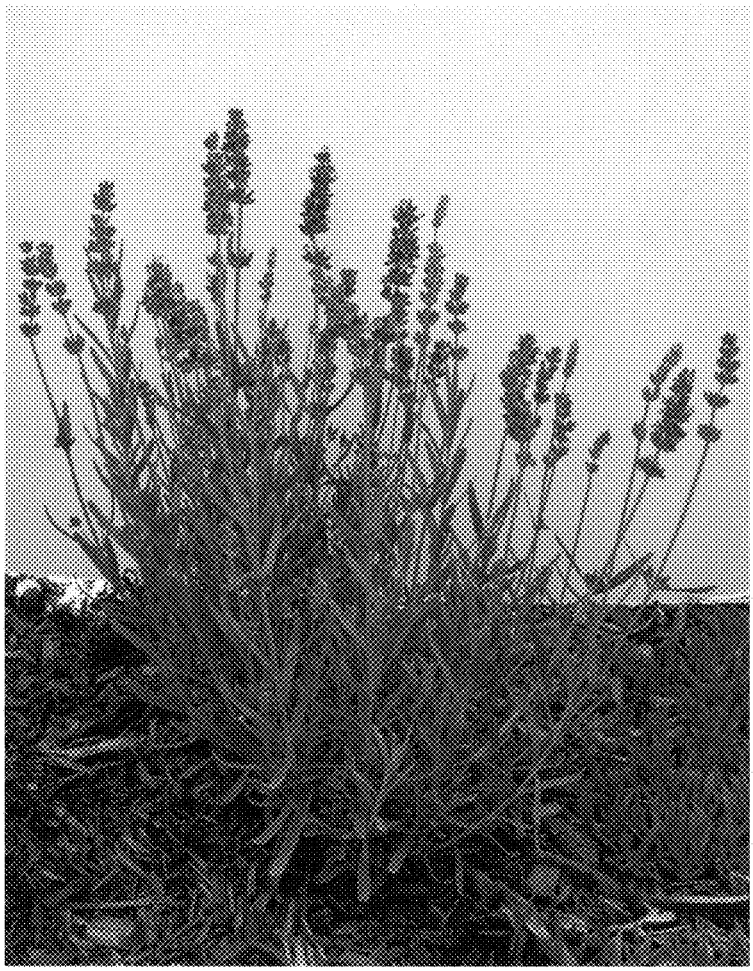
FIG. 1 illustrates a side view of the overall growth and flowering habit of 'SuperBlue'.
Figure 2:
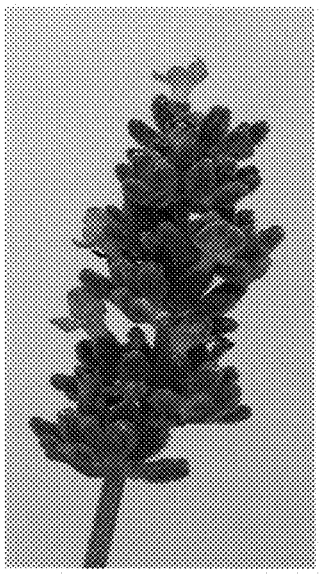
FIG. 2 illustrates a close-up view of an individual inflorescence of 'SuperBlue'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2012 under natural light conditions in West Chicago, Ill.

The following descriptions and measurements describe plants produced from cuttings from stock plants and grown in a glass-covered greenhouse in one-gallon containers under conditions comparable to those used in commercial practice. Greenhouse temperatures were maintained at approximately 50° F. to 70° F. (10.0° C. to 21.1° C.) during the day and approximately 35° F. to 50° F. (1.7° C. to 10.0° C.) during the night. No supplemental lighting was provided. The plants were transplanted to a field in West Chicago, Ill. and grown for approximately 8 weeks. Measurements and numerical values represent averages of typical plants.

Botanical classification: *Lavandula angustifolia* cultivar SuperBlue.

Parentage:

*Female parent*.—Proprietary *Lavandula angustifolia* breeding selection coded 1313-01, not patented.

*Male parent*.—Proprietary *Lavandula angustifolia* breeding selection coded 1254-01, not patented.

Propagation:

*Type cutting*.—Terminal stem.

*Time to initiate roots*.—Approximately 2 weeks.

*Time to produce a rooted cutting*.—Approximately 8 weeks.

*Root description*.—Fine, fibrous; white in color.

*Rooting habit*.—Freely branching, dense.

Plant description:

*Commercial crop time*.—Approximately 14 to 16 weeks from a rooted cutting to finish in a one-gallon container.

*Growth habit and general appearance*.—Moderately vigorous, mounded-compact growth habit.

*Size*.—Height from soil level to top of plant plane: Approximately 37.5 cm. Width: Approximately 48.0 cm.

*Branching habit*.—Freely branching. Quantity of branches per plant: Approximately 12 main and 37 lateral branches.

*Branch*.—Shape: Square in cross section. Strength: Strong. Length: Approximately 34.5 cm. Diameter: Approximately 2.5 mm. Length of central internode: Approximately 2.7 cm. Texture: Densely pubescent. Color of young stems: 137D with 145C at base. Color of mature stems: 137D with 145C at base, base becomes woody 200D with age.

Foliage description:

*General description*.—Quantity of leaves per branch: Approximately 16. Fragrance: Pungent, lavender scent. Form: Simple. Arrangement: Opposite.

*Leaves*.—Aspect: Acute angle to stem. Shape: Lanceolate. Margin: Entire. Apex: Broadly acute. Base: Sessile. Venation pattern: Pinnate. Length of mature leaf: Approximately 4.0 cm. Width of mature leaf: Approximately 5.0 mm. Texture of upper and lower surfaces: Densely pubescent, giving a greyed appearance to foliage. Color of upper surface of young and mature foliage: 137B with midvein of 147C. Color of lower surface of young and mature foliage: 138B with indistinguishable venation.

Flowering description:

*Flowering habit*.—'SuperBlue' is freely flowering under outdoor growing conditions blooming from spring through autumn and with limited flowering under short winter days in a greenhouse environment.

*Lastingness of individual bloom*.—Approximately 10 days.

Inflorescence description:

*General description*.—Type: Single flowers arranged on spikes. Flowers face upright and outwardly. Flowers not persistent. Quantity per plant: Approximately 34. Fragrance: Pungent, lavender scent. Length or height: Approximately 6.0 cm. Width: Approximately 1.7 cm. Quantity of flowers and buds per inflorescence: Approximately 110.

*Peduncle*.—Shape: Square in cross section. Strength: Strong. Aspect: Erect. Length: Approximately 9.5 cm. Diameter: Approximately 2.0 mm. Texture: Densely pubescent, giving a greyed appearance. Color: 137B.

Flower description:

*Type*.—Solitary.

*Bud just before opening*.—Shape: Ovoid. Length: Approximately 5.0 mm. Diameter: Approximately 2.0 mm. Texture: Densely pubescent, colored N92D. Color of bud: 145C, only partially visible under dense pubescence.

*Corolla*.—Shape: Salverform. Flower has a two-lobed upper lip and a three-lobed lower lip. Length: Approximately 1.0 cm. Width: Approximately 4.0 mm.

*Lobes*.—Shape: Ovate. Margin: Entire. Apex: Broadly acute. Length of upper lobes from throat: Approximately 4.0 mm. Width of upper lobes: Approximately 3.0 mm. Length of lower lobes from throat: Approximately 3.0 mm. Width of lower lobes: Approximately 2.0 mm. Texture of upper surface: Sparsely pubescent. Texture of lower surface: Densely pubescent. Color of upper surface when fully open: 90A. Color of lower surface when fully open: 90B.

*Corolla tube*.—Length: Approximately 7.0 mm. Diameter at distal end: Approximately 1.0 cm. Diameter at proximal end: Approximately 1.0 mm. Texture of inner surface: Moderately pubescent. Texture of outer surface: Densely pubescent. Color of inner surface: NN155D with a faint overlay of 90A. Color of outer surface: NN155D with an overlay of 90B.

*Calyx*.—Shape: Tubular. Length: Approximately 5.0 mm. Diameter: Approximately 3.0 mm.

*Sepals*.—Quantity per flower: 5, fused. Shape: Lanceolate. Apex: Acute. Length: Approximately 5.0 mm. Width: Approximately 1.0 mm. Texture of inner surface: Glabrous with dense white-colored pubescence at apex. Texture of outer surface: Densely pubescent, colored N92D. Color of inner surface: 145B. Color of outer surface: 145C, only partially visible under dense pubescence.

*Pedicel*.—Strength: Strong, flexible. Aspect: At an acute angle. Length: Approximately 1.0 mm. Diameter: Less than 1.0 mm. Texture: Densely pubescent. Color: 137B.

*Reproductive organs*.—Androecium: Stamen quantity: 4 per flower, adnate to corolla. Filament length: Approximately 2.0 mm. Filament color: 155D, translucent. Anther shape: Dorsifixed, kidney shaped. Anther length: Less than 1.0 mm. Anther color: N199D with N199B. Pollen amount: Moderate. Pollen color: 21A. Gynoecium: Pistil quantity: 1 per flower. Pistil length: Approximately 5.0 mm. Stigma shape: Oblong. Stigma color: 155D, translucent. Style length: Approximately 3.0 mm. Style color: 145D, translucent. Ovary length: Approximately 1.0 mm. Ovary texture: Glabrous. Ovary color: 144A.

Seed and fruit production: Neither seed nor fruit production has been observed.

Disease and pest resistance: Resistance to pathogens and pests common to *Lavandula* has not been observed.

What is claimed is:

1. A new and distinct cultivar of *Lavandula* plant named 'SuperBlue', substantially as herein shown and described.

* * * * *